(12) United States Patent
Eshoo et al.

(10) Patent No.: US 11,432,750 B2
(45) Date of Patent: Sep. 6, 2022

(54) IN VIVO ENZYME ACTIVITY SENSORS AND METHODS

(71) Applicant: Abbott Diabetes Care, Inc., Alameda, CA (US)

(72) Inventors: Mark Eshoo, San Diego, CA (US); Benjamin Feldman, Berkeley, CA (US); Tianmei Ouyang, Fremont, CA (US); Lam Tran, Dublin, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 359 days.

(21) Appl. No.: 15/457,896

(22) Filed: Mar. 13, 2017

(65) Prior Publication Data

US 2017/0258378 A1    Sep. 14, 2017

Related U.S. Application Data

(60) Provisional application No. 62/308,041, filed on Mar. 14, 2016.

(51) Int. Cl.
*A61B 5/1473* (2006.01)
*C12Q 1/00* (2006.01)
*C12Q 1/46* (2006.01)
*A61B 5/00* (2006.01)
*A61B 5/1486* (2006.01)

(52) U.S. Cl.
CPC ........ *A61B 5/1473* (2013.01); *A61B 5/14865* (2013.01); *A61B 5/7278* (2013.01); *C12Q 1/005* (2013.01); *C12Q 1/46* (2013.01)

(58) Field of Classification Search
CPC .. A61B 5/1473; A61B 5/14735; C12Q 1/004; C12Q 1/005; C12Q 1/46
See application file for complete search history.

(56) References Cited

U.S. PATENT DOCUMENTS

| | | | | |
|---|---|---|---|---|
| 4,525,704 A | * | 6/1985 | Campbell | C12Q 1/005 204/403.1 |
| 4,680,268 A | * | 7/1987 | Clark, Jr. | C12Q 1/005 600/347 |
| 6,245,057 B1 | * | 6/2001 | Sieben | A61B 5/145 424/422 |
| 6,663,615 B1 | * | 12/2003 | Madou | A61K 9/0009 600/345 |
| 2005/0096587 A1 | * | 5/2005 | Santini | A61B 5/4839 604/66 |
| 2007/0060973 A1 | * | 3/2007 | Ludvig | A61B 5/04001 607/45 |
| 2007/0263046 A1 | * | 11/2007 | Iwasa | B01L 3/502715 347/84 |
| 2008/0154179 A1 | * | 6/2008 | Cantor | A61M 37/00 604/20 |
| 2009/0068754 A1 | * | 3/2009 | Wu | A61B 5/14532 436/150 |
| 2011/0014633 A1 | * | 1/2011 | Ifuku | G01N 33/5438 435/7.9 |
| 2012/0296189 A1 | * | 11/2012 | Bhogal | A61B 10/0045 600/365 |

(Continued)

*Primary Examiner* — Daniel L Cerioni
*Assistant Examiner* — Raymond P Dulman
(74) *Attorney, Agent, or Firm* — Sterne, Kessler, Goldstein & Fox P.L.L.C.

(57) ABSTRACT

In vivo monitoring devices and systems for enzymes and/or analytes including devices having a reactant reservoir are provided.

20 Claims, 10 Drawing Sheets

(56) References Cited

U.S. PATENT DOCUMENTS

| | | | |
|---|---|---|---|
| 2013/0211219 A1* | 8/2013 | Coppeta | A61B 5/14532 |
| | | | 600/347 |
| 2017/0258378 A1 | 9/2017 | Eshoo | |
| 2019/0200923 A1* | 7/2019 | Patolsky | A61B 5/1473 |
| 2019/0320947 A1 | 10/2019 | Chen | |

* cited by examiner

IN VIVO ENZYME ACTIVITY SENSORS AND METHODS

CROSS-REFERENCE TO RELATED APPLICATIONS

The present application claims priority to U.S. Provisional Patent Application No. 62/308,041 filed on Mar. 14, 2016, the disclosure of which is incorporated herein by reference.

BACKGROUND

The monitoring of the enzymes, their corresponding activities and their analytes in certain individuals is beneficial to the health and well-being of these individuals. Many disease conditions involve enzymes and/or analytes that may be measured to diagnose the disease state of an individual. In some instances, the concentration level or activity of an enzyme and/or analyte may be useful. In others, the rate of change (increase or decrease) of enzyme and/or analyte level may be diagnostically important.

Electrochemical biosensors based on enzymatic catalysis involve reactions which produce or consume electrons. In such systems, a targeted analyte is involved in a reaction occurring on the surface of an electrode in a suitable sensor, causing the transfer of electrons which may then be measured. Such systems may also be used to detect and measure the presence of substances which inhibit or activate enzymatic activity by measuring changes in the detection of analyte at a sensor. Some enzymes and/or analytes are impracticable or impossible to monitor in vivo using current techniques. One reason for this may be because the concentration is extremely low. Some current in vitro techniques use reactants which are not native in the body and/or are toxic, making adapting them to in vivo testing dangerous. For example, acetylcholinesterase is an enzyme critical for normal nervous system function, but there is no system that monitors it in vivo because its concentration in the body is very low, among other reasons. One method of detecting acetylcholinesterase activity involves assaying the activity of thiocholine in vitro. In this method, acetylthiocholine acts as a substrate for acetylcholinesterase producing thiocholine, which is then detected via oxidation at a suitable electrode. However, because acetylthiocholine is not naturally present (i.e., not native) in the body, this method requires acetylthiocholine to be added to the electrode making continuous, in-vivo monitoring impossible using this technique.

There is a need for devices and methods for in vivo monitoring of enzyme and/or analyte activity.

DESCRIPTION

Figure 1:
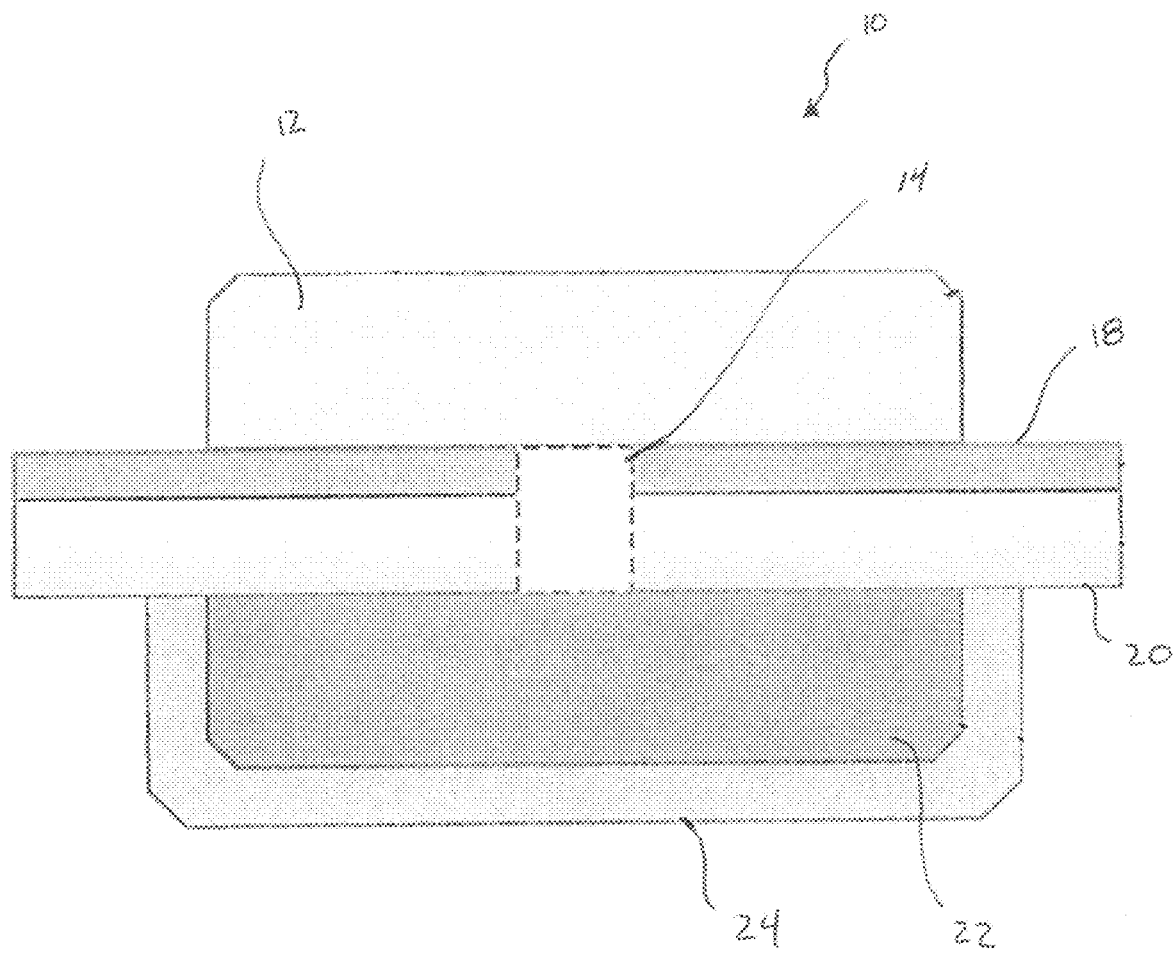
FIG. 1 shows an embodiment of the disclosed technology.

For the purposes of promoting an understanding of the principles of the disclosed technology and presenting its currently understood best mode of operation, reference will now be made to the embodiments illustrated in the drawings and specific language will be used to describe the same. It will nevertheless be understood that no limitation of the scope of the disclosed technology is thereby intended, with such alterations and further modifications in the illustrated devices and systems and such further applications of the principles of the claimed technology as illustrated therein being contemplated as would normally occur to one skilled in the art to which the disclosed technology relates.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 µg, it is intended that the concentration be understood to be at least approximately or about 10 µg.

The presently disclosed technology provides methods and devices and systems for assaying a variety of enzymes or other analytes in vivo. In one method according to the disclosed technology, a reactant is brought into contact with an enzyme at or near an electrode capable of detecting a reaction product of the enzyme and the reactant. The reactant may occur naturally in the subject being tested (i.e., be native) or it may be a naturally occurring or synthetic compound not normally present (i.e., not native) in the subject. The reactant is provided from a storage reservoir or depot which may be disposed on, in or near the electrode or other sensing device. The reactant may be passively or actively caused to contact an enzyme. For example, passive reactant transport may rely in whole or in part on capillary, diffusion or osmosis principles and active reactant transport may rely in whole or in part on a pump or drive mechanism such as a micropump or microvalve. Reactant may be provided from its storage reservoir in a continuous or semi-continuous manner. Embodiments include reactant that is moved along a fluid path automatically so that no action by the user is required to move the reactant. Activity of the enzyme may then be determined using signals generated by the electrode in response to the presence of the reactant-enzyme reaction product. The presence and/or concentration of substances which inhibit or enhance or otherwise modulate the activity of the enzyme may also be determined from the enzyme activity. The storage reservoir may (and/or the reactant itself may be configured to) controllably meter-out or release the reactant over a period of time so that the amount (e.g., concentration, flow rate, etc.) of reactant contacted with the enzyme at any given time is known or fixed, (i.e., predicted or predetermined). A period of time may be at least the wear or useable life of the device that includes the reservoir. When operated on a continuous or semi-continuous basis over time in vivo, such a system may be used to calculate rate and/or direction of change in enzyme activity and/or enzyme inhibitor/enhancer concentrations and/or rates of change and/or direction of change over the period of time of a subject. The continuous or semi-continuous operation may be automatic (e.g., controlled by a processor programmed with instructions to perform the functions).

One example of a device according to the disclosed technology includes a reactant storage reservoir, an enzyme reaction area in fluid communication with the reaction area, and a detection device (such as one or more electrode, optical sensors, and the like). Embodiments include two or more of these elements integrated or combined with a support to form a unitary device. The reactant storage reservoir may be a time-release reservoir and/or the reactant disposed in the reservoir may itself be time-release reactant (e.g., a time-release formulation such as combined with a time release coating, etc.). The exact nature and configuration of the detection device may vary from device to device depending on the requirements of a particular application, but may include electrochemical detection devices or electrodes. In some examples, configurations may include one or more working electrodes with one or more counter electrodes. In other examples, one or more counter electrodes may act as one or more reference electrodes. In still other examples, one or more separate reference electrodes may also be used. An optical detection assembly that may detect an appropriate wavelength of electromagnetic radiation may also be used as a detection device in certain embodiments. An optical detection assembly may include a light emitting device that introduces electromagnetic radiation of an appropriate wavelength to excite a product to produce radiation related to the product, e.g., which may be of a different wavelength, etc. The reflected or transmitted wavelength may be detected.

Detection device placement may be close to or in the same location as the enzyme reaction area. In certain embodiments, a detection device and an enzyme reaction area may be combined into a single element. A detection device may be formed as a solid composition which includes desired components (e.g., an electron transfer agent and/or an enzyme) in a sensing layer. In some embodiments, an enzyme reaction area may be associated with more than one detection device. In some embodiments, these components may be immobilized on the detection device such that they are affixed on the sensor so as to not substantially diffuse away from the working surface of a sensor during the usable life of the sensor (e.g., the period in which the sensor is positioned in a subject for testing purposes before being removed and/or replaced). For example, components, including an enzyme, may be immobilized on a working electrode. The components may be immobilized within or between one or more membranes or films disposed over the working electrode or the components may be immobilized in a polymeric or sol-gel matrix in other examples. In some examples, the reaction area is placed in direct contact with the working electrode and may contain an electron transfer agent to transfer electrons directly or indirectly between the reactant and the working electrode, as well as an enzyme to facilitate a reaction of the reactant. In certain embodiments, electron transfer agent that is present in a subject's body may be utilized, e.g., oxygen. In other examples, the reaction area is not deposited directly on the working electrode, but rather the reaction area may be separated from the working electrode by a separation layer. If employed, such separation layers may include one or more membranes or films. In some embodiments, separation layers may also act as a mass transport limiting layer or an interferent-eliminating layer.

In some examples, a reaction area does not include an electron transfer agent (or it may utilize an endogenous electron transfer agent as described herein), e.g., in certain situations in which the reaction area is spaced apart from the working electrode. In other examples, a reactant reacts with an enzyme to form a product compound (e.g., oxygen) which is electrooxidized or electroreduced at an electrode. Changes in a signal at the electrode indicate changes in the level of product in fluid and are proportional to reactant concentration and/or enzyme activity. In some embodiments, carbon nanotubes and/or multi-walled carbon nanotubes may be included in the reaction area and/or electrode to increase surface area and thereby increase interactions between a reactant and an enzyme.

One or more of the components of a reaction area according to the disclosed technology may be solvated, dispersed, or suspended in a fluid within the reaction area, instead of forming a solid composition. In some embodiments, components which are solvated, dispersed, or suspended in this type of reaction area are immobilized to the reaction area. Such immobilization characteristics may be accomplished, for example, by providing barriers (e.g., membranes, and/or films) around a sensing layer which prevent leaching of components. One example of such a barrier is a microporous membrane or film which allows diffusion of an analyte into a reaction area to make contact with the components of the reaction area, but reduces or eliminates diffusion of reaction area components (e.g., an electron transfer agent, enzyme and/or reactant) out of the reaction area. In certain embodiments, immobilization may be accomplished by molecular forces or bonding so that the enzyme (and/or electron transfer agent) is bound or affixed in way that it is not free to separate from the reaction area.

A reaction area may contain one or more electron transfer agents in communication with conductive material of a working electrode. In some embodiments, there is little or no leaching of an electron transfer agent away from a reaction area during the period in which a sensor is positioned in a patient or test subject. In such examples, material selection and configuration may be used to achieve a desired retention rate of electron transfer agent (e.g., 90%, 95%, 99%, etc.) which remains disposed on a sensor after immersion in fluid to be detected for a desired period of time (as measured in seconds, minutes, hours, days, or months). Electron transfer agents may be bound or otherwise immobilized on a working electrode or disposed between or within one or more membranes or films disposed over working electrodes. Electron transfer agents may be immobilized on working electrodes using, for example, a polymeric or sol-gel immobilization technique or chemically (e.g., ionically, covalently, or coordinately) bound to a working electrode, either directly or indirectly through another molecule, such as a polymer, that is in turn bound to a working electrode.

In some examples of the disclosed technology, electron transfer agents may be electroreducible and electrooxidizable ions or molecules having redox potentials that are a few hundred millivolts above or below the redox potential of a standard calomel electrode (SCE). In some examples, electron transfer agents may not be more reducing than about −150 mV and not more oxidizing than about +400 mV versus SCE. Electron transfer agents suitable for use with the disclosed technology may have structures or charges which prevent or substantially reduce diffusional loss of an electron transfer agent during operation of time of a device. Suitable electron transfer agents may include redox species bound to a polymer which may in turn be immobilized on a working electrode. Bonds between a redox species and a polymer may be covalent, coordinative, or ionic. In some examples, organic or organometallic redox species are bound to a polymer and used as an electron transfer agent (e.g., poly(vinylferrocene)). Suitable polymers may include non-releasable electron transfer agents that are ionically-bound redox species (e.g., a charged polymer coupled to an oppositely charged redox species). Non-releasable electron transfer agents may include redox species that are coordinately bound to a polymer (e.g., coordination of an osmium or cobalt 2,2'-bipyridyl complex to poly(1-vinyl imidazole) or poly(4-vinyl pyridine)). In some examples, a redox species is a transition metal compound or complex such as, for example, transition metal compounds or complexes including osmium, osmium compounds and complexes, ruthenium, iron, and cobalt compounds or complexes.

Suitable non-releasable electron transfer agents may include redox species coordinately bound to a polymer according to some examples of the disclosed technology. In one example, a non-releasable electron transfer agent is formed by coordination of an osmium or cobalt 2,2'-bipyridyl complex to poly(1-vinyl imidazole) or poly(4-vinyl pyridine). In another example, electron transfer agents are osmium transition metal complexes with one or more ligands, each ligand having a nitrogen-containing heterocycle such as 2,2'-bipyridine, 1,10-phenanthroline, or derivatives thereof. Electron transfer agents may have one or more ligands covalently bound in a polymer, each ligand having at least one nitrogen-containing heterocycle, such as pyridine, imidazole, or derivatives thereof. In such examples, electron transfer agents exchange electrons rapidly between each other and working electrodes so that a complex may be rapidly oxidized and reduced. Suitable electron transfer agents in such examples include (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Suitable derivatives of 2,2'-bipyridine for complexation with the osmium cation may include 4,4'-dimethyl-2,2'-bipyridine and mono-, di-, and polyalkoxy-2,2'-bipyridines, such as 4,4'-dimethoxy-2,2'-bipyridine. Suitable derivatives of 1,10-phenanthroline for complexation with the osmium cation may include 4,7-dimethyl-1,10-phenanthroline and mono, di-, and poly-alkoxy-1,10-phenanthrolines, such as 4,7-dimethoxy-1,10-phenanthroline. Suitable polymers for complexation with the osmium cation may include polymers and copolymers of poly(1-vinyl imidazole) (referred to as "PVI") and poly(4-vinyl pyridine) (referred to as "PVP"). Suitable copolymer substituents of poly(1-vinyl imidazole) may include acrylonitrile, acrylamide, and substituted or quaternized N-vinyl imidazole. In some examples, electron transfer agents may be complexed to a polymer or copolymer of poly(1-vinyl imidazole). This listing of electron transfer agents should not be taken as exhaustive and other suitable electron transfer agents may also be used.

Certain embodiments include acetylcholinesterase and a redox polymer (e.g., an osmium redox polymer such as an osmium-decorated poly(vinylpyridine)-based polymer) are crosslinked onto a working electrode of an electrochemical sensor. A depot of time-release acetylthiocholine is added to the sensor and the depot sealed except for an opening that diverts the acetylthiocholine past the crosslinked acetylcholinesterase redox polymer composition in a time release manner.

In examples which employ a membrane for covering an enzyme reaction area and/or regulating flow of reaction from a reaction reservoir, the exact nature of a suitable membrane (or to be used as the enzyme reaction area) will vary depending upon a variety of factors such as the nature of the enzyme or reactant, the size and configuration of a particular device and/or the reactant reservoir, the size and configuration of the aperture(s) in the reactant reservoir, and the location, type, and intended lifecycle of the sensor. In some embodiments, a membrane solution may be made having an appropriate polymer in a solution with an appropriate buffer. Enzymes, electron transfer agents, and other suitable factors may be incorporated into a membrane, as desired, such as by being incorporated into a membrane solution with a polymer, buffer and/or other components for a membrane.

In some embodiments, a reactant storage reservoir (and/or the reactant) is configured to provide for extended release or delivery of a desired amount of reactant over a predetermined period of time so that assays may be made with a device over a desired period of time (minutes, hours, days, months, as desired). In some embodiments, a reactant storage device includes one or more of polymers, membranes, channels such a capillary channel (s), coatings, pores, holes, apertures, and/or mechanical structures (e.g., valves, pumps, and the like) for providing predictable extended delivery times and/or concentrations of a reactant or reactants. Diffusion-control polymers may be used and include, for example, those described herein. Any apertures present in a storage device for delivering reactant to an enzyme reaction area may be configured (e.g., shaped, sized, and the like) to result in prolonged or continuous time-delayed release of reactant from a reactant storage reservoir to an enzyme reaction area over a desired period of time (at least the useable life of the device). A time release profile may be determined, and the reactant and/or storage reservoir may be configured to release reactant according to the time release profile. In certain embodiments, the reactant may be provided to the enzyme so that it is in excess to the enzyme. In certain embodiments, reactant from a reactant storage reservoir may be directed to pass through a suitable coating, membrane, or other layer to reach an enzyme reaction area, where the coating, membrane, or other layer that is passed through regulates release of the reactant to the enzyme reaction area over a desired period of time. In some examples, systems include an osmotic delivery system or a microfluidics delivery system. For example, a reactant storage reservoir may be combined with an osmotic delivery system and/or combined with a microfluidics delivery system which provides extended delivery of reactant to an enzyme reaction area to provide a desired extended release/time profile.

An enzyme may be associated with an enzyme reaction area by covalent or non-covalent interactions as desired. In some embodiments, an enzyme may be attached using appropriate linkers, spacers, and/or cross-linkers. An enzyme may be attached to a support using, for example, glutaraldehyde as a crosslinking agent, or oxidation of oligosaccharide groups of the enzyme with NaIO4, followed by coupling of the aldehydes formed to hydrazide groups in a polyacrylamide matrix to form hydrazones. Other chemistries suitable for attaching enzymes to a support may also be used. An enzyme reaction area may include a surface or layer with which the enzyme(s) are associated, such as a polymer or gel layer. Such a gel layer may be any biocompatible, nontoxic, and immunogenically compatible polymer.

Device supports and/or structures may be formed using a variety of non-conducting materials, including, for example, polymeric or plastic materials and ceramic materials. Suitable materials for a particular device may be determined, at least in part, based on the desired use of the device and properties of the component materials. Suitable materials include, for example, poorly conducting ceramics, such as aluminum oxide and silicon dioxide, non-conducting plastic or polymeric materials and other non-conducting, flexible, deformable materials, thermoplastics such as polycarbonates, polyesters, polyvinyl chloride (PVC), polyurethanes, polyethers, polyamides, polyimides, or copolymers of these thermoplastics, such as PETG (glycol-modified polyethylene terephthalate).

In some devices, a protective layer is formed over at least the portion of the detection device(s), at least a portion of the detection device is positioned beneath a skin surface of patient subject. This layer may serve one or more functions, such as biomolecule size exclusion preventing penetration of large biomolecules into or near electrodes such as a working electrode, preventing protein adhesion to a device, and preventing formation of blood clots, biofilms, and other undesirable interactions between a device and body. For example, the body-inserted portions of a device may be completely or partially coated with a biocompatible coating. In some examples, a biocompatible coating is a hydrogel which contains at least 20 wt. % fluid when in equilibrium with an analyte-containing fluid. Examples of suitable hydrogels may include crosslinked polyethylene oxides, such as polyethylene oxide tetraacrylate, and the like.

Some devices according to the disclosed technology may be configured as devices designed for automatic in vivo monitoring of an enzyme and/or analyte such that at least a portion of the device is positioned beneath a skin surface of an individual to perform the monitoring, e.g., over time. Such devices may include a distal end which is to be positioned in vivo into a patient and may have a width of 2 mm, 1 mm, 0.5 mm, or less. In such examples, the device may or may not have regions of different widths and the overall width of such a device may be, for example, 2 mm, 1.5 mm, 1 mm, 0.5 mm, 0.25 mm, or less. Such devices may be wider or narrower as desired.

Devices and systems according to the disclosed technology may include one or more of a temperature sensor, a power supply, a communication unit, a data processing unit, a data storage unit, a display unit, an audible output unit, a power source (e.g., a battery), and/or a vibratory output unit. In some examples, a communication unit sends and/or receives signals between a device and a communications unit on a second device, e.g., a smart phone, other hand held device, and/or computer. Such communication units may receive instructions from a second device. Other examples of devices include a structure or component suitable for attaching the device to a subject. Examples include an adhesive pad for positioning and attaching a device to a subject, a belt, clasp, and/or tie for attaching a device to a subject. In other examples, a device comprises a mechanism for attaching to an article of clothing worn by a patient or to a mounting stand or bracket.

Devices and systems according to the disclosed technology may have a plurality of parts, including, for example, in vivo positionable sensors (e.g., a subcutaneous sensor) and a sensor control unit, wherein the sensor control unit may be coupled (physically or wirelessly) to the sensor. A sensor control unit may be physically attached to the sensor at the sensor's proximal end, which may be positioned outside the body of the user while the distal sensor end may be positioned inside the user's body. A sensor control unit may be attached to the skin of the patient. A sensor control unit operates a connected sensor, including, for example, providing a voltage across the electrodes of the sensor and collecting signals from the sensor. Some sensor control units may evaluate signals from a sensor and/or transmit signals to one or more receiver/display units for evaluation. In some embodiments, a sensor control unit and/or the receiver/display units display or otherwise communicate current level(s) of one or more analytes and/or enzymes measured to one or more other devices, e.g., a smart phone, other hand held device, and/or a computer. In some embodiments, the sensor control unit receives instructions from one or more other devices. In still other examples, other devices such as computers are configured to receive communication signals from more than one sensor and/or sensor control units concurrently, such as in a hospital where a device is configured to receive signals from sensors applied to multiple patients. Sensor control units and/or receiver/display units may include audible, visual, or other sensory-stimulating alarm, when the level of an analyte and/or enzyme is at or near one or more predetermined threshold level(s). In some embodiments, tactile stimuli such as an electrical shock, vibration, or the like may be delivered to the subject as a warning.

Devices according to the disclosed technology may be utilized in a variety of conditions. The exact circumstances and steps for using such a device may vary according to a variety of factors such as the analyte(s) being measured, the desired duration of the monitoring, the size and configuration of a particular device, and the like. For example, a device may include a sensor at least a portion of which is configured for in vivo positioning into a subject for a desired period of time. Such a sensor may be positioned in the interstitial tissue for testing of interstitial fluid, in the dermal space for testing of dermal fluid, and the like. For example, the interstitial or dermal measurements—as the case may be—may be correlated and/or converted into analyte levels in the blood or other fluids. In other examples, sensors may be positioned in other regions of the body to measure other fluids. For example, a sensor may be positioned in the arterial or venous systems for direct testing of blood or positioned into the spinal canal to measure cerebral spinal fluid. Examples of using devices according to the disclosed technology may therefore be altered to suit the appropriate circumstances of a particular application.

A variety of different methods and systems may be employed which utilize devices according to the disclosed technology to measure and/or monitor a desired analyte. For example, reactants for enzymes may be converted to products that include a reporter or are a reporter. Such reporters may be detected and/or measured electrochemically or optically by a device. In other examples, a desired enzyme may be detected and/or measured, either directly or indirectly, by a device. In certain embodiments, the activity level of an enzyme and/or change in activity level over time may be used to determine the presence and/or concentration of a substance which inhibits or enhances the enzyme's activity. A drop in signal caused by decreased enzyme activity may be correlated with the concentration of an enzyme inhibitor and an increase in signal caused by increased enzyme activity may be correlated to the concentration of an enzyme enhancer.

Two or more enzymes may be used by a device to detect and/or monitor a desired analyte level according to the disclosed technology. In one example, a first enzyme reacts with a reactant to make a first product. This first product reacts with a second enzyme to make a second product that may then be detected electrochemically by the device. In some embodiments, the two or more enzymes may both be associated with a device (such as by being loaded into one, or optionally separate storage reservoirs), and a device is used to detect an analyte that reacts sequentially with the enzymes to produce a reaction product that may be detected electrochemically. In some embodiments, at least one of the two or more enzymes is associated with a device, and at least one enzyme is found in bodily fluid. In these examples, a device detects the one or more enzyme(s) in bodily fluid. In some embodiments, the enzyme(s) in bodily fluid enters an enzyme reaction area of a device where it reacts with a reactant to produce a reaction product which reacts with the one or more enzymes associated with the device to produce a reporter that may then be detected electrochemically.

In certain embodiments, the in vivo devices may be used to monitor a subject's exposure to a chemical or agent (e.g., an organophosphate) for a desired period such as days or weeks when a subject may be at risk or at least suspected of being at risk for possible exposure to a chemical or an agent. For example, a worker in a pesticide factory, a technician cleaning a chemical spill, or a soldier in a combat zone, and the like may wear a device of the subject disclosure at least during their stay in a potentially contaminated area and in certain embodiments before and/or afterwards. Such devices may also be used to monitor a patient after a confirmed exposure to a harmful agent, e.g., following an acute exposure to a chemical or agent, and devices may be used to monitor changes in the levels of chemicals and/or agent(s) in a subject automatically and continuously over time. For example, a device may be used to monitor a subject's response to anti-agent drugs and/or procedures administered to the subject to treat acute exposure to an agent. Additionally, a device may be used to personalize treatment so that a subject receives adequate treatment to remediate their particular amount or degree of exposure to an agent. For example, disclosed are devices, systems and methods for monitoring drug targets in vivo, e.g., enzymes that are targets of drugs. An enzyme target may be inhibited (or increased) by a drug consumed by a subject. In certain embodiments, the subject devices, methods and systems may be used to assess the drug interaction of the enzyme acetylcholinesterase and the drug donepezil (a brand name is Aricept), and the assessment may be utilized to customize the drug therapy (e.g., dosage). Donepezil reversibly inhibits acetylcholinesterase from hydrolyzing acetylcholine, which, in turn, increases the availability of acetylcholine to the brain and strengthens nerve signals. Embodiments include providing a reactant (e.g., acetylthiocholine) in a storage reservoir and releasing the reactant so it reacts with the acetylcholinesterase, which may be associated with a working electrode of an electrochemical sensor, e.g., which may be crosslinked with a redox polymer such as an osmium decorated redox polymer. The activity of the enzyme may be monitored (e.g., a product of the reaction such as thiocholine). Thiocholine may be oxidized by the redox polymer (e.g., the electron transfer agent such as osmium), to produce current. When donepezil is present in a subject's body, thiocholine production is curtailed and current drops. Data from a comparison of the original (non-donepezil) current with the donepezil-present current can be utilized to modulate donepezil dosage for the particular subject.

Some examples of enzyme-drug pairings that may be utilized by the technology disclosed herein include:

TABLE 1

| | |
|---|---|
| Aldehyde dehydrogenase | Disulfiram |
| Monoamine oxidases (MAOs) | Tranylcypromine, moclobemide Tranylcypromine |
| Cyclooxygenases (COXs) | Acetylsalicylic acid, profens, acetaminophen and dipyrone (as arachidonylamides) |
| | Acetylsalicylic acid, profens, acetaminophen and dipyrone (as arachidonylamides) |
| Vitamin K epoxide reductase | Warfarin, phenprocoumon |
| Aromatase | Exemestane |
| Lanosterol demethylase (fungal) | Azole antifungals |
| Lipoxygenases | Mesalazine Zileuton |
| Thyroidal peroxidase | Thiouracils |
| Iodothyronine-5' deiodinase | Propylthiouracil |
| Inosine monophosphate dehydrogenase | Mycophenolate mofetil |
| HMG-CoA reductase | Statins |
| 5α-Testosterone reductase | Finasteride, dutasteride |
| Dihydrofolate reductase (bacterial) | Trimethoprim |
| Dihydrofolate reductase (human) | Methotrexate, pemetrexed |
| Dihydrofolate reductase (parasitic) | Proguanil |
| Dihydroorotate reductase | Leflunomide |
| Enoyl reductase (mycobacterial) | Isoniazid |
| Squalene epoxidase (fungal) | Terbinafin |
| Δ14 reductase (fungal) | Amorolfin |
| Xanthine oxidase | Allopurinol |
| 4-Hydroxyphenylpyruvate dioxygenase | Nitisinone |
| Ribonucleoside diphosphate reductase | Hydroxycarbamide |
| Protein kinase C | Miltefosine |
| Bacterial peptidyl transferase | Chloramphenicol |
| Catecholamine-O-methyltransferase | Entacapone |
| RNA polymerase (bacterial) | Ansamycins |
| Reverse transcriptases (viral) | Zidovudine Efavirenz |
| DNA polymerases | Acyclovir, suramin |
| GABA transaminase | Valproic acid, vigabatrin |
| Tyrosine kinases | Imatinib Erlotinib Sunitinib Sorafenib |
| Glycinamide ribonucleotide formyl transferase | Pemetrexed |
| Phosphoenolpyruvate transferase (MurA, bacterial) | Fosfomycin |
| Human cytosolic branched-chain aminotransferase (hBCATc) | Gabapentin |
| Aspartyl proteases (viral) | Saquinavir, indinavir |
| Unspecific | Aprotinine |
| Bacterial serine protease | β-lactams |
| Bacterial serine protease | Glycopeptides |
| Bacterial lactamases | Sulbactam |
| Human antithrombin | Heparins |
| Human plasminogen | Streptokinase |
| Human coagulation factor | Factor IX complex, Factor VIII |
| Human factor Xa | Fondaparinux |
| Human ACE | Captopril |
| Human HRD | Cilastatin |
| Human carboxypeptidase A (Zn) | Penicillamine |
| Human enkephalinase | Racecadotril |
| 26S proteasome | Bortezomib |
| Esterases | Physostigmine Obidoxime Caffeine Amrinon, milrinone Papaverine Sildenafil Valproic acid Carbamezepine |
| Glycosidases (viral) | Zanamivir, oseltamivir |
| Glycosidases (human) | Acarbose |

TABLE 1-continued

| | |
|---|---|
| Lipases | Orlistat |
| Phosphatases | Cyclosporin |
| | Lithium ions |
| GTPases | 6-Thio-GTP (azathioprine metabolite) |
| Phosphorylases | Bacitracin |
| DOPA decarboxylase | Carbidopa |
| Carbonic anhydrase | Acetazolamide |
| Histidine decarboxylase | Tritoqualine |
| Ornithine decarboxylase | Eflornithine |
| Soluble guanylyl cyclase | Nitric acid esters, molsidomine |
| Alanine racemase | D-Cycloserine |
| DNA gyrases (bacterial) | Fluoroquinolones |
| Topoisomerases | Irinotecan |
| | Etoposide |
| Δ8,7 isomerase (fungal) | Amorolfin |
| Dihydropteroate synthase | Sulphonamides |
| Thymidylate synthase (fungal and human) | Fluorouracil |
| Thymidylate synthase (human) | Methotrexate, pemetrexed |
| Phosphofructokinase | Antimony compounds |
| mTOR | Rapamycin |
| Haem polymerase (Plasmodium) | Quinoline antimalarials |
| 1,3-β-D-glucansynthase (fungi) | Caspofungin |
| Glucosylceramide synthase | Miglustat |

Devices according to the disclosed technology may be used to detect analytes or enzymes in fluid from the interstitial space, dermal space, serum, blood, cerebral spinal fluid, or other compartments of the body. Such devices may be positioned in vivo subcutaneously (including partially positioned (transcutaneously) and wholly positioned), intravenously, intraperitoneally, intramuscularly, intraspinally, or otherwise positioned into the subject's body as desired. Devices according to the disclosed technology may be used to automatically detect absolute analyte levels, relative analyte levels, changes in analyte levels, rates of change in analyte levels, and/or crossing of predetermined threshold analyte level(s) according to a schedule (continually or semi-sontinually).

Monitored subjects may include humans or other animals such as canine, feline, porcine, bovine, murine, ovine, capra, equine, or other commercially valuable livestock. In some examples a plurality of subjects may be monitored by devices which communicate with a central location where data from sensors is analyzed to provide population-based information. Additional information may also be provided by a device such as location information (e.g., GPS information), and population data may be combined with such location information. Data from such population-distributed devices may be combined with other measurements made on subjects to detect, diagnose, research, describe, or study population-based phenomenon. Additional data combined with sensor data may include, for example, location, heart rate, respiratory rate, lactate, blood pressure, and/or other metabolite levels. In some examples, at least some of the plurality of subjects are in a hospital and/or being transported. In these examples, central monitoring of subjects may reduce response times and reduce time for the initiation of therapies.

Reactant Storage

Devices according to the disclosed technology may include one or more reactant storage reservoirs for the reactants that are released over an extended period of time. The exact size and configuration of such reservoirs may vary according to the analyte being tested for, the intended duration of the testing, the conditions under which the testing will occur, and the like. In some examples, a reactant storage reservoir includes one or more of a coating, membrane, aperture, mechanical device, osmotic device, pump, or the like for extending or regulating the delivery of reactant from the storage reservoir. The exact size and nature of such delivery moderators will vary according to the nature of the enzyme or reactant being delivered and the desired dosage profile (rate and/or amount) and may be formed by such methods as etching, laser machining, mechanical machining, drilling, etc. Examples of dose-moderating membranes or coating materials may include polymer dispersions such as polyurethane dispersions, acrylic latex dispersions, copolymers of acrylates, and the like.

In other examples, a storage reservoir includes a diffusion-controlling polymer. Examples of such polymers may include hyaluronic acid, poly(ethylene glycol), phosphoryl choline based polymers and other hydrophilic polymers having a hydrophilicity comparable to HA, PEG, or phosphoryl choline, ethylene vinyl alcohol copolymer, polyhydroxyalkanoate, poly(hydroxyvalerate), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid) (DLPLA), poly(ortho esters), poly(glycolic acid-co-trimethylene carbonate), polyphosphoester, polyphosphoester urethane, poly(amino acids), cyanoacrylates, poly(trimethylene carbonate), poly(iminocarbonate), polyurethanes, copoly (ether-esters) (e.g. PEO/PLA), polyalkylene oxalates, polyphosphazenes, biomolecules, such as fibrin, fibrinogen, cellulose, starch, collagen and hyaluronic acid, polyurethanes, silicones, polyesters, polyolefins, polyisobutylene and ethylene-alphaolefin copolymers, acrylic polymers and copolymers, vinyl halide polymers and copolymers, poly(amide ester) (PEA), polycaprolactone (PCL), poly(hexafluoro propylene) (HFP), poly(ethylene vinyl alcohol) (EVAL), polyvinyl ethers such as polyvinyl methyl ether, polyvinylidene halides such as polyvinylidene fluoride (PVDF) and polyvinylidene chloride, polyacrylonitrile, polyvinyl ketones, polyvinyl aromatics such as polystyrene, polyvinyl esters such as polyvinyl acetate, copolymers of vinyl monomers with each other and olefins such as ethylene-methyl methacrylate copolymers, acrylonitrile-styrene copolymers, ABS resins, and ethylene-vinyl acetate copolymers, polyamides such as Nylon 66 and polycaprolactam, alkyd resins, polycarbonates, polyoxymethylenes, polyimides, polyethers, epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. In some examples, a suitable drug eluting polymer is a copolymer comprising a poly(ethylene glycol terephthalate) and poly(butylene terephthalate) (PEGT/PBT) segments.

Further examples of polymers include, without limitation, polycarboxylic acids, cellulosic polymers, gelatin, polyvinylpyrrolidone, cross-linked polyvinylpyrrolidone, polyanhydrides including maleic anhydride polymers, polyvinyl alcohols, polyvinyl aromatics such as copolymers of polystyrene with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyether sulfone, polyalkylenes including polypropylene, polyethylene and high molecular weight polyethylene, halogenated polyalkylenes including polytetrafluoroethylene, natural and synthetic rubbers including polyisoprene, polybutadiene, polyisobutylene and copolymers thereof with other vinyl monomers such as polyorthoesters, proteins, polypeptides, siloxane polymers, polylactic acid, polyglycolic acid, polyhydroxybutyrate valerate and blends and copolymers thereof as well as other biodegradable, bioabsorbable and biostable polymers and copolymers. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In other examples, suitable polymers include polyacrylic acid and a copolymer of polylactic acid and polycaprolactone. In certain embodiments, the reactant in the storage reservoir may be a time release formulation and/or include a time release coating.

Reactant storage reservoirs may provide delivery of a reactant (egress of reactant to an area outside the reservoir) by an osmotic delivery system, such as an electroosmotic pump system or elementary osmotic pump (EOP) system. In some examples, a reactant storage reservoir includes water-soluble compounds suitable for inducing osmosis, i.e. osmotic agents or osmogents, including pharmaceutically acceptable and pharmacologically inert water-soluble compounds. In some examples, an osmotic agent is a pharmaceutically acceptable water-soluble salt of inorganic or organic acids, or non-ionic organic compounds with high water solubility, e.g., carbohydrates such as sugar, or amino acids. Osmotic agents may include inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like, and mixtures thereof. The amount of osmogents that may be used depends on the particular osmogent being used and may range from about 1% to about 60% by weight of the reactant mixture in certain embodiments. An osmotic delivery system may also include a polymer, such as those described above as drug eluting polymers, and/or a coating and/or membrane acting as a semipermeable barrier between an enzyme and a reactant. In certain embodiments, a reactant storage reservoir includes or is part of a microfluidics systems for delivering a reactant to an enzyme.

Enzymes, Reporters and Reactant-Reporter Conjugates

In some examples of the disclosed technology, a reporter is a moiety capable of being detected indirectly or directly. Examples of suitable reporters may include, a redox reporter, a chromophore, a fluorophore, a bioluminescent protein, a fluorescent protein, a receptor, a hapten, an enzyme, and a radioisotope. Reporters may detect the amount of an enzyme or the amount of an analyte, as desired. A reporter may be any detectable moiety, including, without limitation, a redox molecule, isotope, chromophore, or fluorophore. In some examples, a reporter is a fluorescent reporter, a bioluminescent reporter, or other optical reporter. A reporter may be conjugated to an enzyme reactant and released from a reactant by the action of the enzyme. In other examples, a reporter is an enzyme reactant and when an enzyme acts on the reactant it is converted to an active form of the reporter.

Enzyme activities that may be detected and measured by or used in a sensor of the disclosed technology may include acetylcholinesterase, alkaline phosphatase, chloramphenicol acetyltransferase, peroxidase, β-lactamase, aldehyde dehydrogenase, monoamine oxidase, cyclooxygenase, Vitamin K epoxide reductase, aromatase, lanosterol demethylase, lipoxygenase, thyroidal peroxidase, iodothyronine-5'-deiodinase, inosine monophosphate dehydrogenase, HMG-CoA-reductase, 5-α-testosterone reductase, dihydrofolate reductase, dihydroorotate reductase, enoyl reductase, squalene epoxidase, xanthine oxidase, 4-hydroxyphenylpyruvate dioxygenase, ribonucleoside diphosphate reductase, protein kinase C, catecholamine-O-methyltransferase, GABA transaminase, or tyrosine kinase.

Reactants paired with aceyticholinesterase may include, for example, acetylthiocholine. Reactants paired with alkaline phosphatase may include, for example, p-aminophenyl phosphate, PNPP (p-Nitrophenyl Phosphate, Disodium Salt), 1,2-dioxetane chemiluminescent reactant. Redox reactants paired with peroxidase may include, for example, hydroquinone, hydroxymethyl ferrocene, osmium complex, p-aminophenol, m-aminophenol, and o-aminophenol (o-AP). Other example reactants for peroxidase may include, for example, ABTS (2,2'-Azinobis [3-ethylbenzothiazoline-6-sulfonic acid]-diammonium salt), OPD (o-phenylenediamine dihydrochloride), TMB (3,3',5,5'-tetramethylbenzidine), SuperSignal ELISA Pico Chemiluminescent Substrate, QuantaBlu NS/K Fluorogenic Substrate, QuantaRed Enhanced Chemifluorescent HRP Substrate (ADHP), Amplex Red reagent. Redox reactants paired with β-lactamase may include, for example, C3' thiolate-substituted cephalosporins. In some embodiments, other reactants for β-lactamase may include, for example, CCF2-FA, CCF2-AM, and CCF4-AM.

Suitable enzyme-reactant pairs may include, for example, aldehyde dehydrogenase-appropriate aldehyde and/or NAD+(for NAD dependent aldehyde dehydrogenases), monoamine oxidase-appropriate monoamine, cyclooxygenase-ascorbate, lipoxygenase-linoleic acid, thyroidal peroxidase-iodide ions and thyroglobulin, iodothyronine-5'-deiodinase-thyroxine, HMG-CoA-reductase-HMG-CoA and NADPH, 5-α-testosterone reductase-testosterone (or other reactant) and NADPH, dihydrofolate reductase-dihydrofolic acid and NADPH, squalene epoxidase-squalene and NADPH, and xanthine oxidase-hypoxanthine.

EXAMPLES

The technology disclosed herein will be better understood from the experimental details which follow. However, one skilled in the art will readily appreciate that the specific methods and results discussed are merely illustrative of the technology as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

Example 1

In Vivo Enzyme Detection Device

FIG. 1 depicts one example of an in vivo enzyme detection device 10 according to the disclosed technology. The device 10 includes a storage reservoir or depot 22, a support 20, a working electrode 18, an aperture 14, and a layer 12 (e.g., a polymer layer) which includes an enzyme and may also include an electron transfer agent. Layer 12 may be a redox polymer. The storage reservoir 22 is defined at least partially by walls or impermeable barrier 24 so that reactant can only egress from the reservoir through aperture 14. That is, reactant is released from the storage reservoir 22 through aperture 14 in the support 20 which forms part of the storage reservoir 22. The reactant is released (e.g., controllably or predictably) over time through the aperture 14 into the layer 12 where the reactant reacts with the target enzyme. The reaction product produced by the enzyme and reactant then reacts with either the electron transfer agent (if present in layer 12 or another), or directly interacts with the electrode to produce a signal. The signal produced will be proportional to the enzymatic activity. Certain embodiments include an enzyme such as acetylcholinesterase and a redox polymer (e.g., an osmium redox polymer such as an osmium-decorated poly(vinylpyridine)-based polymer or other poly(vinylpyridine)-based polymer) crosslinked together and immobilized to the working electrode of an electrochemical sensor. A depot of time-release reactant such as acetylthiocholine is positioned in or on the sensor and the depot sealed except for the aperture that diverts flow or egress of the reactant acetylthiocholine past the crosslinked acetylcholinesterase redox polymer composition in a time release manner.

In certain embodiments, a sensor does not include an enzyme in layer 12, and instead fluid from the subject or sample tested contains the enzyme. For example, reactant from a storage reservoir diffuses through a polymer layer, and into the surrounding fluid or fluid sample. There, reactant interacts with an enzyme, producing a product that may then diffuse back to the electrode, or to an electron-transfer agent located near the electrode, and be detected electrochemically. This particular embodiment assays the subject's own native enzyme.

In another embodiment, a sensor does not include an enzyme in layer 12, and instead enzyme from the test subject or sample tested contains an enzyme. For example, an enzyme enters a reaction area from the patient or sample, where it reacts with a reactant from a storage reservoir. This reaction of enzyme and reactant produces a reaction product which is detected by an electrode (or product that interacts with an electron transfer agent which is detected by an electrode). A signal produced at the electrode will be proportional to the quantity of enzyme in the subject and/or sample.

In another embodiment, an analyte in a test subject or sample inhibits or inactivates the activity of an enzyme in a polymer layer. The degree of inhibition which occurs in a sensor will be proportional to the amount of analyte in the subject or sample. In some embodiments, an analyte in the subject enhances activity of an enzyme to produce signal above the baseline from the reactant that is released from a storage reservoir. The degree of additional signal from an electrode will be proportional to the analyte level in the subject or the sample.

Example 2

Detection of Organophosphate

Figure 2:
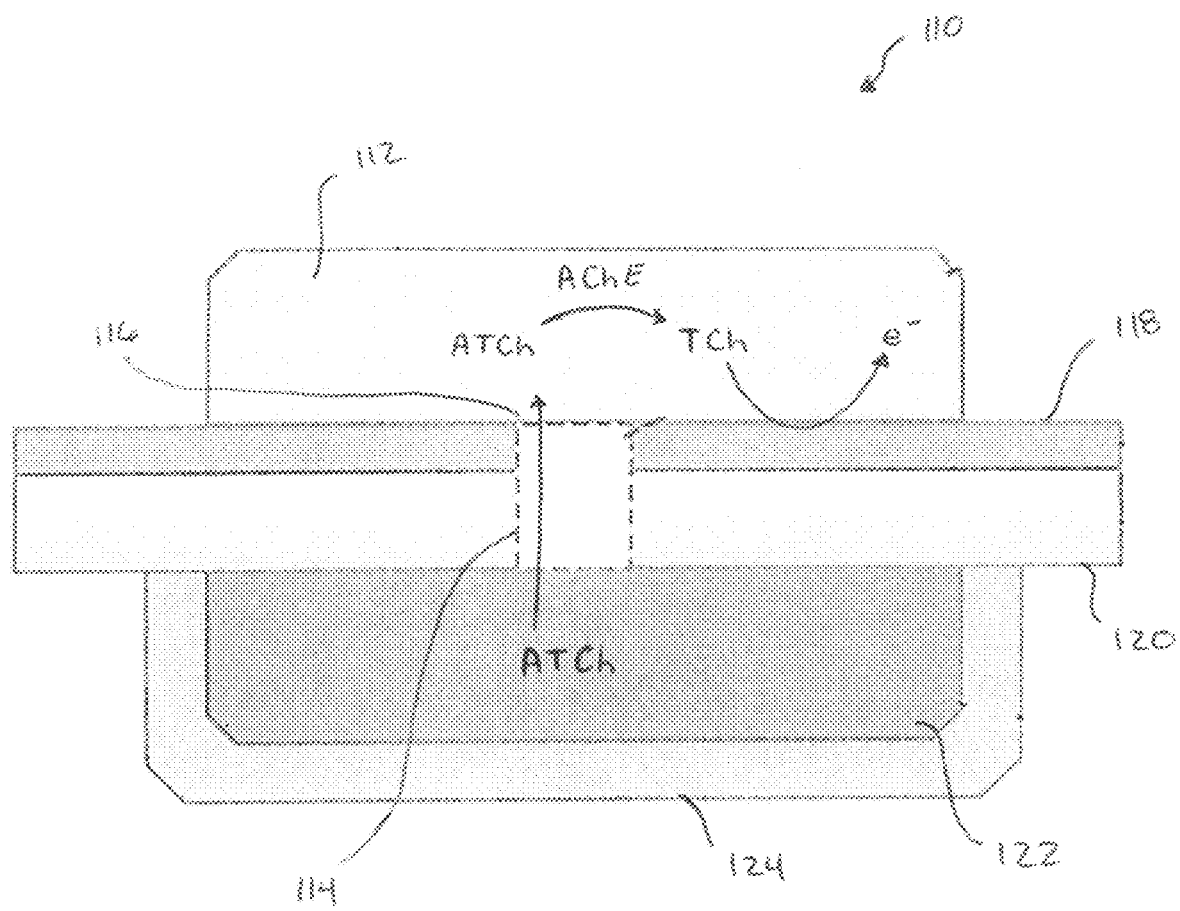
FIG. 2 shows an example of normal operation of an embodiment of the disclosed technology.
Figure 3:
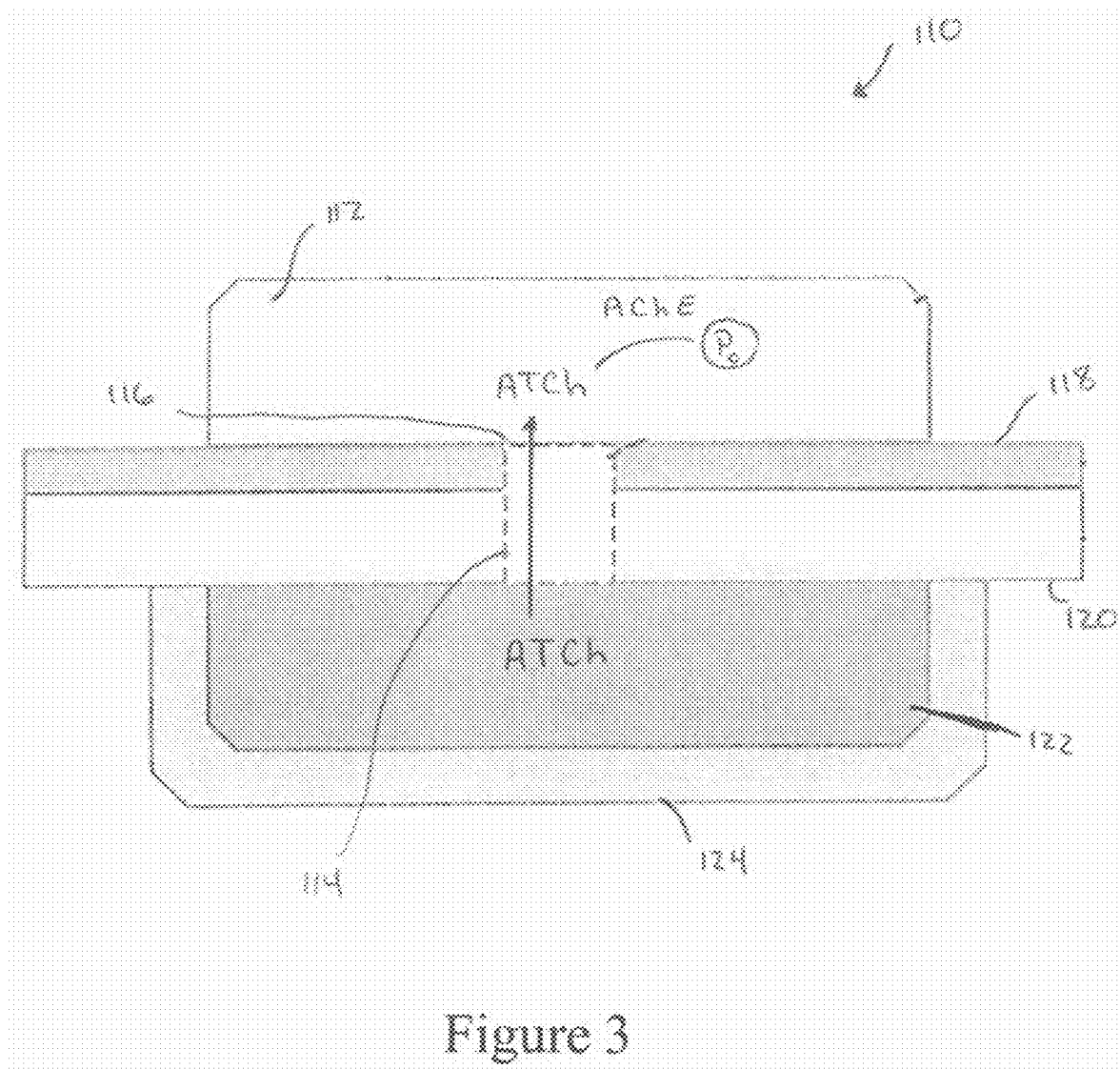
FIG. 3 shows an example of exposed operation of the embodiment of FIG. 2.

FIGS. 2-3 show an example of a device like that shown in FIG. 1 designed and configured to detect organophosphates (Po). In this particular example, a device 110 includes a support 120 and a storage reservoir 122 bound at least partially by an impermeable barrier layer 124 filled with acetylthiocholine (ATCh). During normal operation and over time such as an hour or more (i.e., with no organophosphates present), ATCh diffuses through an aperture 114 in the support 120 into a layer 112 which includes an enzyme such as acetylcholinesterase (AChE) and may include an electron transport agent (e.g., an osmium complex), and which may be a polymer layer (e.g., a redox polymer). In some embodiments, ATCh release is rate controlled. For example, aperture 114 may include a rate control member (valve, microfluidics device, semi-permeable membrane, pump, etc). In this embodiment, membrane 116 is shown which limits the rate at which the ATCh may diffuse from the reservoir 122. When in the enzyme layer 112, the ATCh acts as a reactant substrate and is cleaved by AChE, producing thiocholine (TCh), which is then detected electrochemically at an electrode 118 formed on the support layer 120. The TCh may be oxidized by the redox polymer, producing electrochemical current. So long as the TCh is present in relative excess, the resulting current will be proportional to the enzymatic activity of the immobilized enzyme AChE.

A number of organophosphate compounds act as acetylcholinesterase inhibitors. In the presence of organophosphate compounds as seen in FIG. 3, production of thiocholine is diminished or eliminated as the acetylcholinesterase bonds with organophosphate compounds and is prevented from cleaving acetylthiocholine into thiocholine. Consequently, detection (e.g., current) of thiocholine at the electrode decreases. In this example, organophosphate exposure is indicated by a decrease of output current at the electrode. In other examples, a device may be configured to detect a pre-determined absolute signal level to signify organophosphate exposure. In other examples, a device may be configured to signal when a pre-determined change or rate of change in activity is detected.

Example 3

In Vivo Acetylcholinesterase Devices

Figure 4:
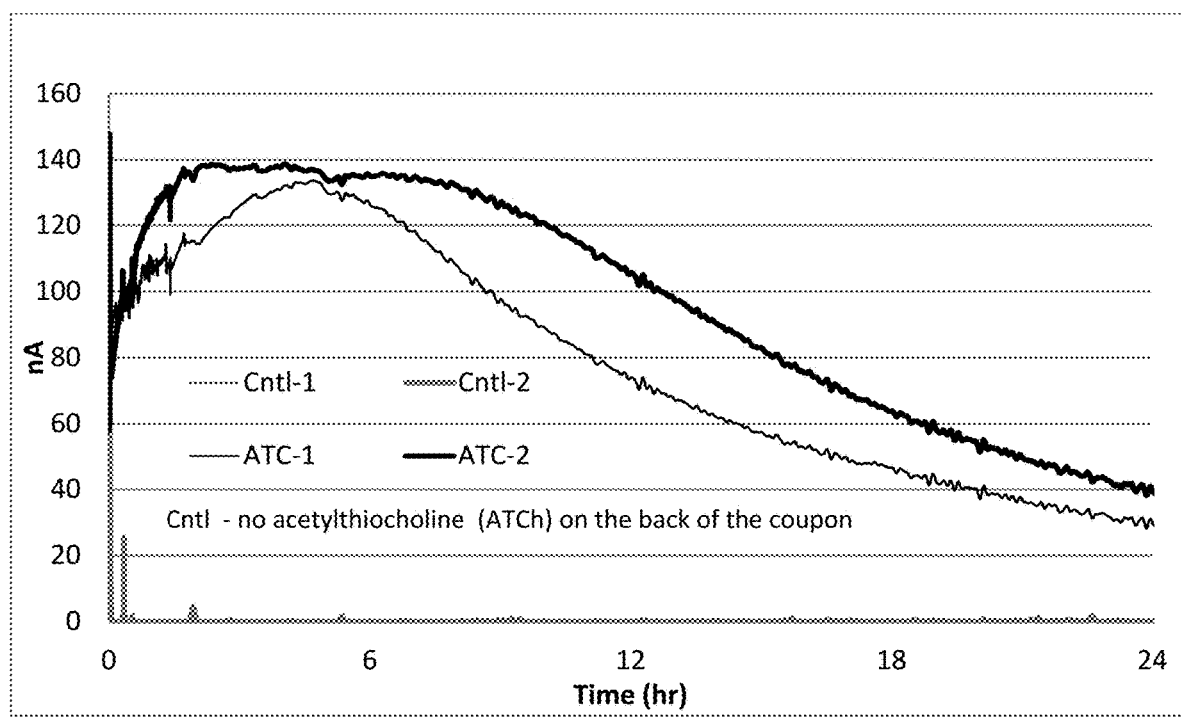
FIG. 4 shows a redox reaction at a sensing electrode for an embodiment of the disclosed technology.

In this example, devices similar to that from Example 1 were used. The enzyme AChE was immobilized in a redox polymer layer crosslinked with PEG400 crosslinker, reactant acetylthiocholine is placed in a storage reservoir on each sensor. FIG. 4 is graph of the signal obtained when operating the example devices for 24 hours. The devices indicated by ATC-1 and ATC-2 show a strong, detectable signal from the devices that slowly decay over the 24 hour period of testing. Controls 1 and 2 (no acetylthiocholine) show no or little signal over the 24 hour testing period.

Example 4

In Vivo Acetylcholinesterase Electrodes

Figure 5:
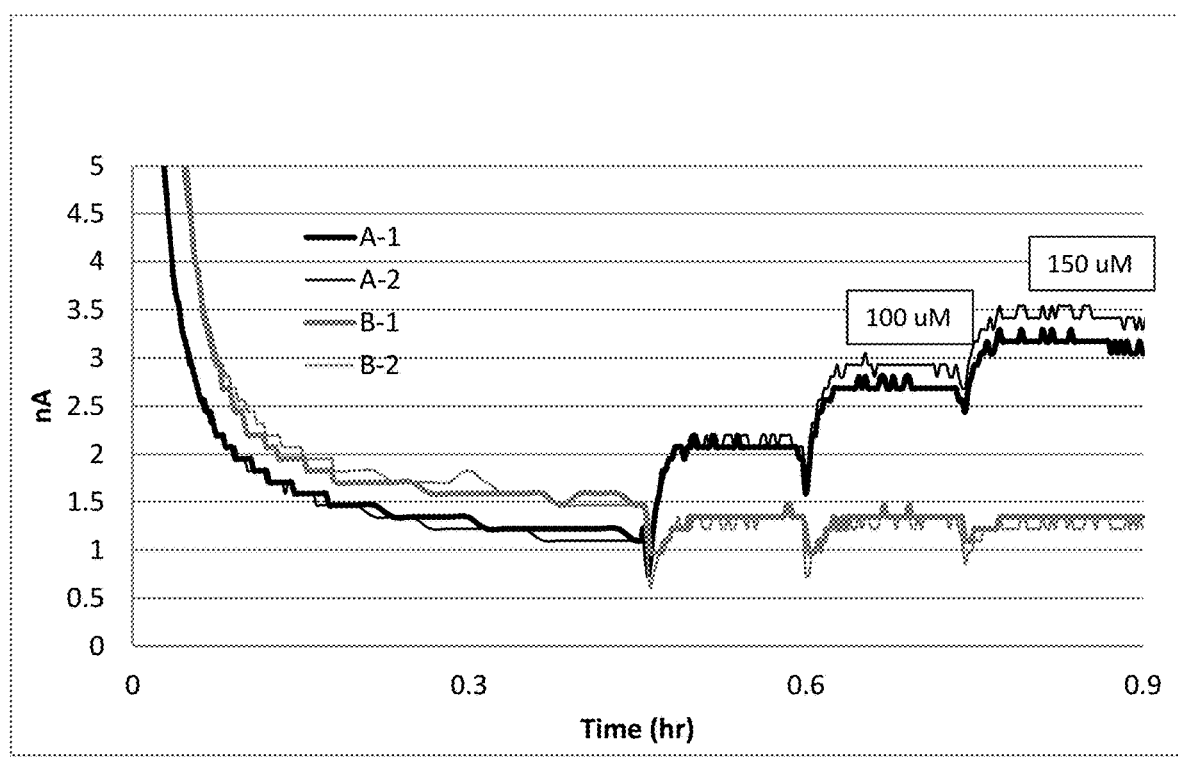
FIG. 5 shows a redox reaction at sensing electrodes according to one embodiment of the disclosed technology as compared to control electrodes.

In this example, electrodes according to the disclosed technology were compared to control electrodes. The electrodes prepared according to the disclosed technology each included a working electrode coated with a mixture of crosslinked redox polymer and AChE (electrodes A-1 and A-2). Control electrodes each having a working electrode coated with a crosslinked redox polymer but no AChE were also prepared (electrodes B-1 and B-2). The electrodes were then bathed in a PBS buffer solution and exposed to increasing concentrations of acetylthiocholine over time as shown in FIG. 5. Electrodes A-1 and A-2 responded to acetylthiocholine in the solution as the immobilized acetylcholinesterase on the electrodes cleaved the acetylthiocholine to produce thiocholine, which was detected by the electrodes.

Example 5

Multi-Aperture Reactant Reservoir

Figure 6:
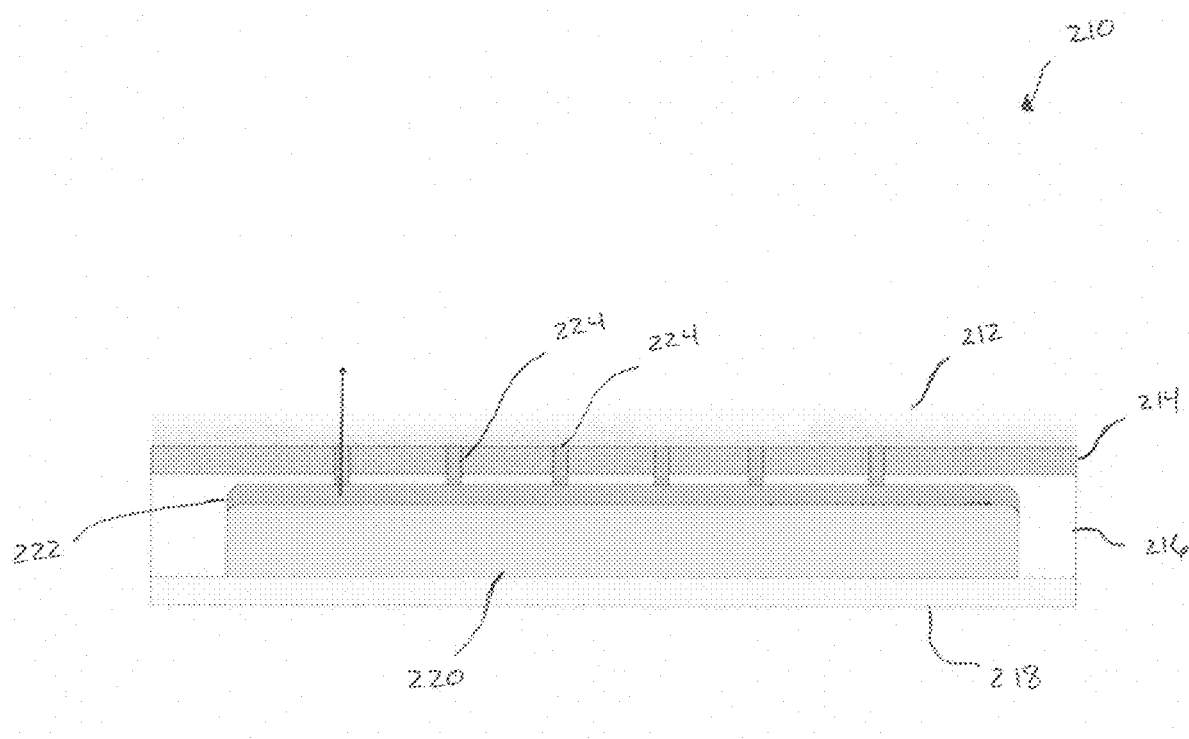
FIG. 6 shows an embodiment of the disclosed technology.

FIG. 6 shows another example of a device according to the disclosed technology. In this example, a device 210 includes a storage reservoir 220 disposed within a support 216 which is mounted to a working electrode 214. The reservoir 220 is bounded on one side by a backing 218. In some embodiments, the reservoir 220 is filled with a reactant prior to application of the backing 218. In other examples, the backing 218 may be mounted to the reservoir 220 prior to adding a reactant. A plurality of apertures 224 passing through the working electrode 214 connect the reservoir 220 to a reaction area 212 proximate to a surface of the working electrode 214. The number, size, shape, and configuration of the apertures 224 may vary as desired to best suit a particular application. In other examples, the reaction area 212 may include a membrane, polymer layer, or other egress rate-modulating element, as previously described. In some embodiments, a membrane layer 222 disposed within a portion of the reservoir 220 and/or the apertures 224 may be used to regulate dispersal of the reactant into the reaction area 212.

Example 6

Electrode with Reactant Reservoir

Figure 7:
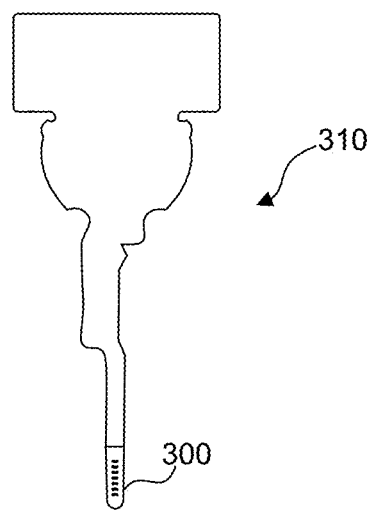
FIG. 7 shows an embodiment of the disclosed technology.
Figure 8:
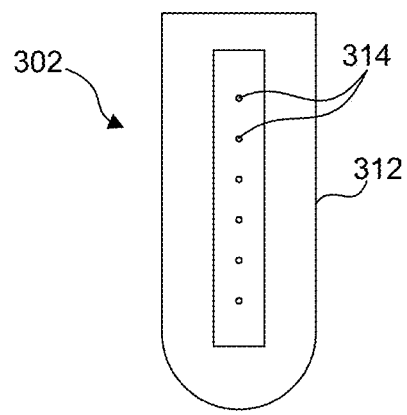
FIG. 8 shows an enlarged view of a portion of the embodiment shown in FIG. 7.
Figure 9:
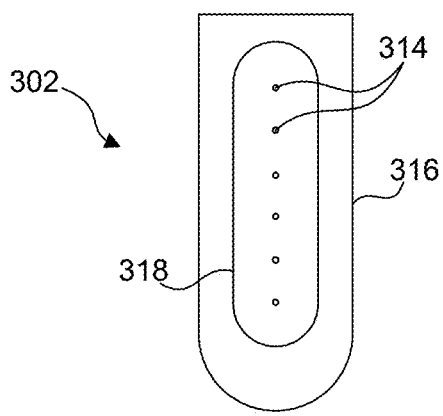
FIG. 9 shows another view of the embodiment shown in FIG. 8.
Figure 10:
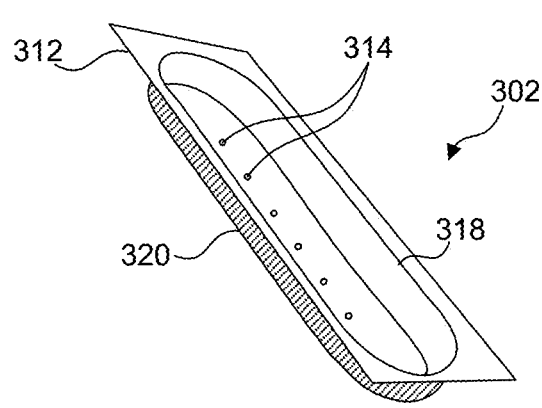
FIG. 10 shows a perspective view of the embodiment shown in FIG. 9.

In the example shown in FIGS. 7-10, a reactant reservoir according to the disclosed technology has been formed partially within the body of an electrode. A sensor 310 having a working electrode 300 tip is shown in FIG. 7, although the disclosed technology may be applied to a variety of different electrode styles and configurations. Structures may be formed using a suitable material on the surface of the electrode to increase the potential surface area for a reactant to interact with an analyte and/or enzyme. A reactant reservoir 302 as seen in FIGS. 8-10 was formed in the material 316 of electrode 300. A variety of suitable techniques may be used to form such a feature such as laser engraving or scribing, chemical etching, sputtering, and the like. In some embodiments, the electrode may include a reservoir when initially formed. The exact size, shape, and configuration of such a reservoir may vary according to the requirements of a particular application.

FIG. 8 shows the front face 312 of the reservoir 302 which includes a plurality of apertures 314 for allowing reactant to be released from the reservoir 302 in proximity to the electrode 300. The exact number, size, shape, location, and configuration of apertures may vary according to the requirements of a particular application. FIG. 9 shows the back of the reservoir 302 which is being shown without a backing or cover for purposes of clarity. The reservoir 302 includes a storage chamber or depot 318 where a quantity of reactant may be stored. Once filled, the back of the reservoir 302 may be closed using a membrane or other suitable material. In some embodiments, the back of the reservoir may be closed prior to adding reactant to the storage chamber which is accomplished such as by adding it through the apertures. In this particular example, the side walls 320 of the reservoir 302 have been formed from the material 316 of the electrode 300. In other examples, some portion or all of the side walls may be formed from material added to an electrode such as previously described.

In one embodiment, a reservoir was formed by laser scribing a depot in the back of electrode material. New material to complete the reservoir was a screen printed double walled carbon nanotube layer on white PET, which provides a higher current for acetylthiocholine detection. This particular reservoir design had the dimensions of ~180 µm depth, 2 mm length, and 150 µm width. The sensor being used had a width of 1500 µm. To release acetylthiocholine to the front of the electrode, apertures were laser drilled to various diameters of 10-50 µm.

This particular enzyme sensor was capable of providing a slow, predicable release of acetylthiocholine for a period of 1-2 days to weeks. The reservoir design included a mediating or time-release membrane that regulated diffusion of acetylthiocholine out of the reservoir to the front of the electrode. The formulation used poly(vinylpyridine) and Poly(ethylene glycol) diglycidyl ether. The membrane was deposited after the reservoir had been laser scribed. The Acetylthiocholine formulation contained up to 300 nL of 1 M Acetylthiocholine with or without 0.1% surfactant. The back of the depot was closed by the addition of a breathable polyurethane adhesive having a low water vapor permeability. For beaker testing with acetylcholinesterase in solution, the electrode was dipped in 5% fluoropolymer for stability.

Example 7

In Vivo Acetylcholinesterase Sensor

Figure 13:
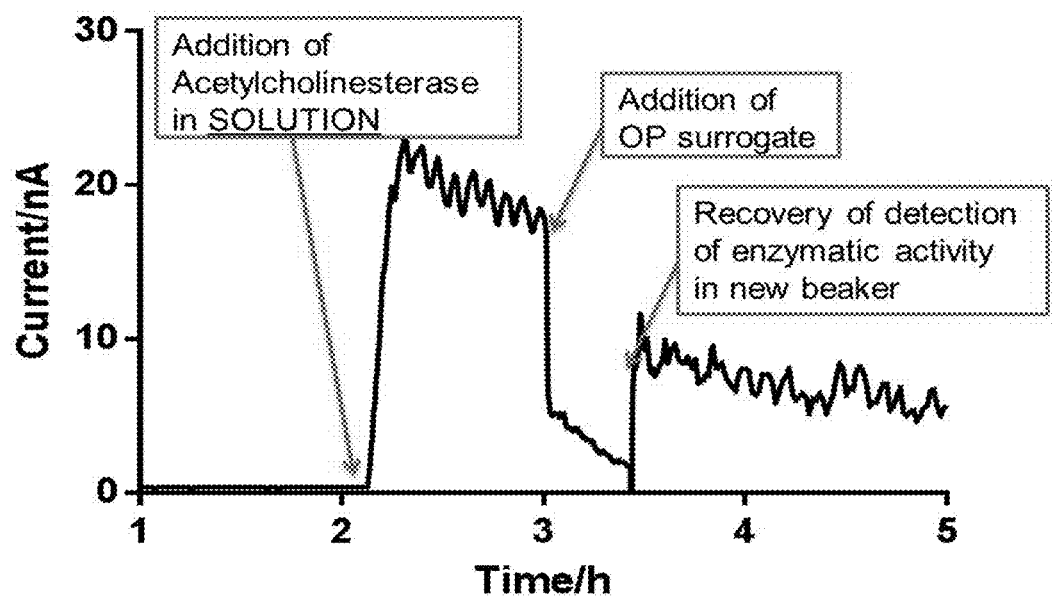
FIG. 13 shows a redox reaction at a sensing electrode for an embodiment of the disclosed technology described in Example 7.

In this example, a buffer was created to simulate endogenous cholinesterase activity in the interstitial fluid of a test subject. A sensor similar to that described in Example 6 was created with 100 nL of 1 M acetylthiocholine in the reactant reservoir. The sensor was placed in a buffer solution of 20 mM PBS, pH 7.4, and 1 U/mL of acetylcholinesterase enzyme to simulate a test subject. A reversible acetylcholinesterase inhibitor (Neostigmine Bromide) was then added to the buffer solution to simulate an organophosphate. The sensor was then removed from the buffer solution containing the inhibitor and placed in fresh buffer solution. The resulting profile shown in FIG. 13 indicates where the initial signal created by acetylcholinesterase interacting with acetylthiocholine from the sensor fell off after the addition of the inhibitor. Once the sensor was removed from the solution containing the inhibitor the signal rebounded as acetylcholinesterase began once again cleaving acetylthiocholine.

Example 8

In Vivo Sensor Electrode with Reactant Reservoir

Figure 11:
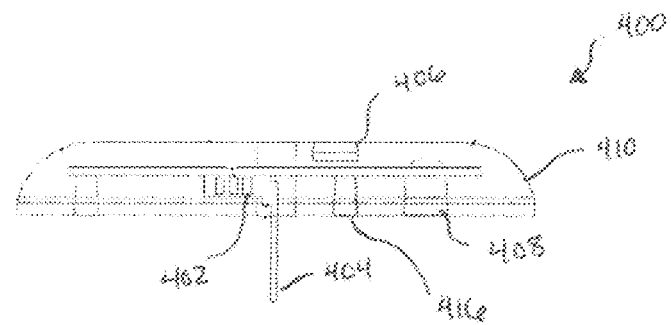
FIG. 11 shows a partial cross sectional view of another embodiment of the disclosed technology.
Figure 12:
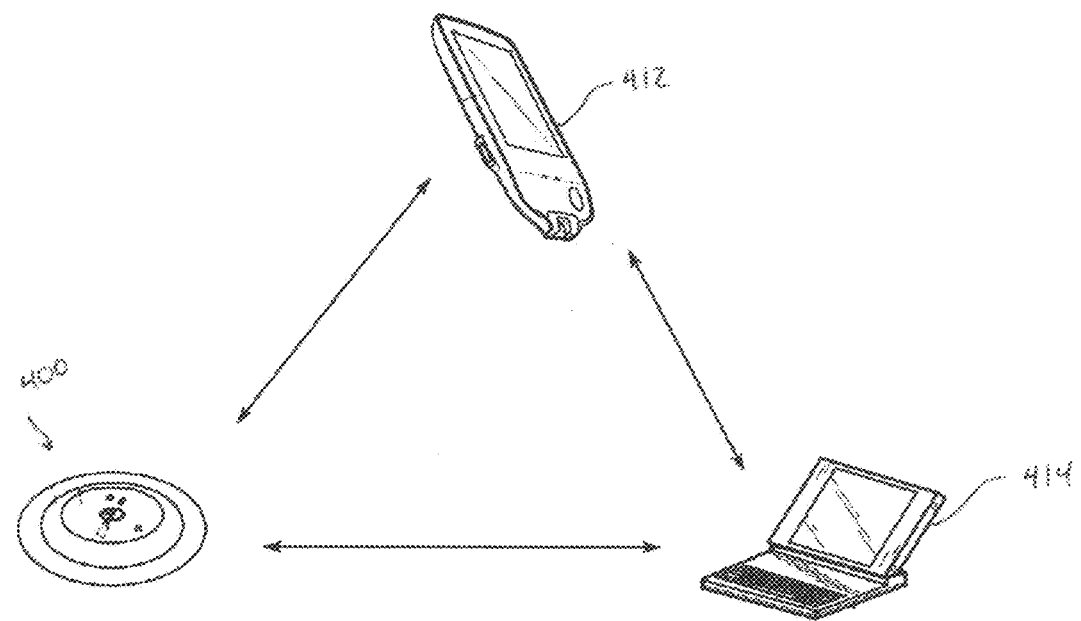
FIG. 12 shows the embodiment of FIG. 11.

In the example shown in FIGS. 11-12, a sensor 402 having an electrode 404 with a reactant reservoir according to the disclosed technology has been incorporated into a wearable device 400. The embodiments described herein may be configured as that which is shown in FIGS. 11-12. The device also includes a power source 416 such as a battery, a memory storage component 408, and a communication component 406, all of which may be operationally connected to the sensor 402. A device housing 410 encompasses and protects the components of the device 400 and includes a body-attachment element (e.g., an adhesive surface) to allow it to be worn for an extended period of time by a subject.

The device 400 may operate on an automatic basis and store data on the memory unit 408 continuously or semi-continuously. The device may transfer such data automatically or only on-request to one or more separate data processing units 412, 414. A variety of devices may serve as processing units such as computers 414, purpose-built hand-held devices 412, smartphones, and the like. These devices may be configured to communicate directly with a wearable device 400, with one another, or both. Such communication may be accomplished using a variety of wired or wireless protocols such as Bluetooth, NFC, RFID, and the like, and may take the form of one or more discrete transmissions (either concurrent or consecutive), a continuous or semi-continuous transmission, or combinations thereof. The devices may be configured to receive signals from a single sensor or from a plurality of sensors on one or more test subjects. A sensor may be a no-user calibration sensor in that it does not require calibration to be performed by a user. Calibration may be factory-set.

Example 9

In Vivo Sensor Electrode with Reactant Reservoir

Figure 14:
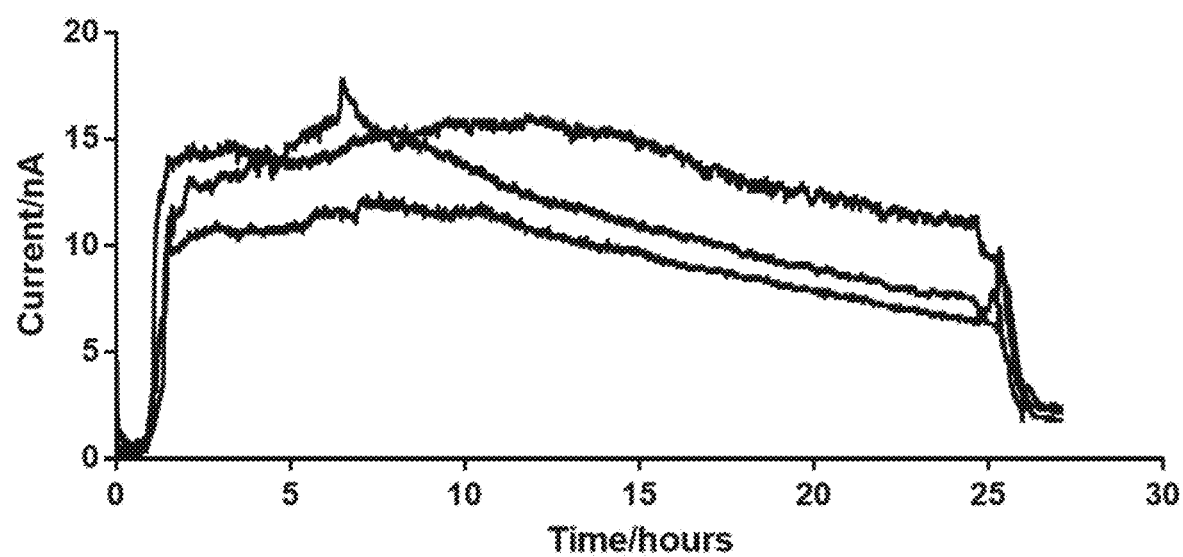
FIG. 14 shows a redox reaction at a sensing electrode for an embodiment of the disclosed technology described in Example 9.

In this example, a sensing enzyme for created using multi-walled carbon nanotubes, AChE, PVI polymer, and PEG400. A reactant reservoir prepared with 200 nL of this solution on prepared electrodes and cured at 25° C. and 60% humidity for 24 hours, then dipped in a 5% sulfonated tetrafluoroethylene based fluoropolymer-copolymer solution. The reactant reservoir also included 300 nL 1 M acetylthiocholine with 0.05% surfactant. The electrode was placed in a beaker containing 20 mM PBS at 7.4 pH. The graph below represents elution of acetylthiocholine after 1 hour in the beaker. The sensor produced a relatively stable current over a period of 24 hours after which an organophosphate surrogate was added to the beaker. The acetylthiocholine was inhibited by the surrogate and the electrochemical signal decreased in response as seen in the graph shown in FIG. 14. The signal failed to return after 30 minutes of exposure to the surrogate.

All publications, patents and patent applications discussed and cited herein are incorporated herein by reference in their entireties. It is understood that the disclosed technology is not limited to the particular methodology, protocols and materials described as these may vary. It is also understood that the terminology used herein is for the purposes of describing particular embodiments only and is not intended to limit the scope of the disclosed technology which will be limited only by the appended claims. Those skilled in the art will recognize, or be able to ascertain using no more than routine experimentation, many equivalents to the specific embodiments of the disclosed technology described herein. Such equivalents are intended to be encompassed by the following claims.

What is claimed is:

1. A continuous in vivo apparatus for determining the activity of an enzyme in vivo, comprising:
   a detection device comprising one or more working electrodes;
   a reaction area comprising the enzyme, the reaction area in fluid communication with the detection device and placed in contact with the one or more working electrodes;
   a storage reservoir containing a predetermined quantity of a reactant;
   at least one aperture passing through the one or more working electrodes, wherein the at least one aperture connects the storage reservoir to the reaction area proximate to a surface of the one or more working electrodes;
   wherein the storage reservoir passively provides the reactant to the reaction area only through egress from the at least one aperture;
   wherein the one or more working electrodes are configured to detect a product of a reaction of the reactant and the enzyme in the reaction area; and
   wherein at least a portion of the reaction area and the storage reservoir are implantable into a tissue.

2. The apparatus of claim 1, wherein the reactant is acetylthiocholine and the enzyme is acetylcholinesterase.

3. The apparatus of claim 1, wherein at least a portion of the storage reservoir is formed on or within a support layer.

4. The apparatus of claim 3, wherein the at least one aperture further passes through the support layer.

5. The apparatus of claim 1, wherein the at least one aperture further comprises a regulator to control a release of the reactant from the storage reservoir over a predetermined period of time.

6. The apparatus of claim 5, wherein the regulator is a membrane.

7. The apparatus of claim 1, wherein the reaction area further comprises a polymer layer containing the enzyme.

8. The apparatus of claim 7, wherein the enzyme is crosslinked to the polymer layer.

9. The apparatus of claim 8, wherein the polymer layer comprises a redox polymer.

10. The apparatus of claim 9, wherein the redox polymer is an osmium redox polymer.

11. The apparatus of claim 10, wherein the osmium redox polymer is osmium poly(4-vinyl pyridine).

12. The apparatus of claim 1, wherein the enzyme within the reaction area is immobilized to the one or more working electrodes.

13. A continuous in vivo apparatus for determining the activity of an enzyme in vivo, comprising:
    a storage reservoir containing a predetermined quantity of a reactant;
    a working electrode comprising at least one aperture; and
    a reaction layer arranged on the working electrode, wherein the reaction layer comprises an enzyme;
    wherein the reactant is passively released from the storage reservoir through the at least one aperture of the working electrode, wherein the working electrode is configured to detect a product of a reaction of the reactant with the enzyme in the reaction layer in order to produce a signal proportional to the activity of the enzyme, and
    wherein at least a portion of the apparatus is configured to be positioned beneath a skin surface.

14. The apparatus of claim 13, wherein the reaction layer comprises a polymer layer containing the enzyme.

15. The apparatus of claim 13, wherein the reaction layer further comprises an electron transfer agent.

16. The apparatus of claim 13, wherein a support layer defines at least a portion of the storage reservoir.

17. A continuous in vivo apparatus for determining the activity of an enzyme in vivo, comprising:
    a working electrode comprising at least one aperture;
    a storage reservoir containing a predetermined quantity of a reactant, wherein the storage reservoir is arranged on a first side of the working electrode; and
    a reaction layer comprising an enzyme, wherein the reaction layer is arranged on an opposing, second side of the working electrode,
    wherein the reactant is configured to be passively released through the at least one aperture of the working electrode such that the reactant reacts with the enzyme in the reaction layer, and wherein the working electrode is configured to detect a product of a reaction of the reactant and the enzyme in the reaction layer.

18. The apparatus of claim 17, wherein at least a portion of the apparatus is configured to be positioned beneath a skin surface.

19. The apparatus of claim 17, further comprising a support layer defining at least a portion of the storage reservoir.

20. The apparatus of claim 17, wherein the reaction layer further comprises an electron transfer agent.

* * * * *